(12) United States Patent
Richardson et al.

(10) Patent No.: US 10,031,140 B1
(45) Date of Patent: Jul. 24, 2018

(54) ORTHOGONAL SAW TRANSDUCERS ON SUBSTRATE FOR SIMULTANEOUS BIOFOULING REMOVAL AND BIOSENSING

(71) Applicants: Mandek Brishen Richardson, Tampa, FL (US); Venkat Rama Bhethanabotla, Tampa, FL (US)

(72) Inventors: Mandek Brishen Richardson, Tampa, FL (US); Venkat Rama Bhethanabotla, Tampa, FL (US)

(73) Assignee: University of South Florida, Tampa, FL (US)

( * ) Notice: Subject to any disclaimer, the term of this patent is extended or adjusted under 35 U.S.C. 154(b) by 157 days.

(21) Appl. No.: 15/006,852

(22) Filed: Jan. 26, 2016

Related U.S. Application Data (60) Provisional application No. 62/107,787, filed on Jan. 26, 2015.

(51) Int. Cl.
  *G01N 29/02* (2006.01)
  *G01N 29/22* (2006.01)
  *G01N 33/543* (2006.01)

(52) U.S. Cl.
  CPC ..... *G01N 33/54393* (2013.01); *G01N 29/022* (2013.01); *G01N 29/221* (2013.01); *G01N 33/54306* (2013.01); *G01N 33/54366* (2013.01)

(58) Field of Classification Search
  None
  See application file for complete search history.

(56) References Cited

U.S. PATENT DOCUMENTS

| | | | | |
|---|---|---|---|---|
| 6,304,021 | B1 * | 10/2001 | Wolf | B08B 3/12 310/313 B |
| 7,398,685 | B2 * | 7/2008 | Itoh | B01F 11/0266 73/54.41 |
| 7,878,063 | B1 | 2/2011 | Cular | |
| 8,018,121 | B1 | 9/2011 | Cular | |
| 8,508,742 | B2 | 8/2013 | Charette | |
| 2010/0162815 | A1 * | 7/2010 | Lee | G01N 29/022 73/579 |
| 2010/0271188 | A1 * | 10/2010 | Nysen | G01S 13/755 340/10.41 |

(Continued)

OTHER PUBLICATIONS

L.A. Francis, C. Bartic, A. Campitelli, J.M. Friedt; A SU-8 liquid cell for surface acoustic wave biosensors; proceedings of SPIE—The interntational Society of Optical Engineering; Aug. 2004.*

(Continued)

*Primary Examiner* — Daniel J Colilla
(74) *Attorney, Agent, or Firm* — Thomas | Horstemeyer, LLP (57) ABSTRACT

Devices and methods for use in removing non-specific binding in a bioassay are disclosed. A substrate can be used with input and output transducers to output surface acoustic waves. The surface acoustic waves can be transmitted through a medium. One of the input and output transducers can be formed on the surface of the substrate aligned with an x-axis of the substrate. These input and output transducers can excite a Rayleigh surface acoustic wave through the medium. Another one of the input and output transducers can be formed orthogonal to the x-axis. These input and output transducers can excite a shear wave.

20 Claims, 6 Drawing Sheets

(56) References Cited

U.S. PATENT DOCUMENTS

2017/0184581 A1* 6/2017 Larson ............. G01N 33/54373

OTHER PUBLICATIONS

Cular, Stefan, et al. "Acoustic manipulation of biological samples for improved sensors." AIChE Annual Meeting, Conf. Proc. 2005.
Branch, Darren W., and Susan M. Brozik. "Low-level detection of a Bacillus anthracis simulant using Love-wave biosensors on 36 YX LiTaO 3." Biosensors and Bioelectronics 19.8 (2004): 849-859.
Gronewold, Thomas MA, et al. "Discrimination of single mutations in cancer-related gene fragments with a surface acoustic wave sensor." Analytical chemistry 78.14 (2006): 4865-4871.
Konstantinos Mitsakakis and Electra Gizeli, "Detection of multiple cardiac markers with an integrataed acoustic platform for cardiovascular risk assessment." Analytica Chimica Acta (2011), p. 1-5.
Onen, Onursal, et al. "A urinary Bcl-2 surface acoustic wave biosensor for early ovarian cancer detection." Sensors 12.6 (2012): 7423-7437.
Schlensog, Marc D., et al. "A Love-wave biosensor using nucleic acids as ligands." Sensors and Actuators B: Chemical 101.3 (2004): 308-315.
Lange, Kerstin, Bastian E. Rapp, and Michael Rapp "Surface acoustic wave biosensors: a review." Analytical and bioanalytical chemistry 391.5 (2008): 1509-1519.
Moriizumi, T., Y. Unno, and S. Shiokawa. "New sensor in liquid using leaky SAW." IEEE 1987 Ultrasonics Symposium. IEEE, 1987.
Gizelli, E., et al. "Surface skimming bulk waves: a novel approach to acoustic biosensors." Solid-State Sensors and Actuators, 1991. Digest of Technical Papers, Transducers'91., 1991 International Conference on. IEEE, 1991.
Berkenpas, Eric, et al. "Pure shear horizontal SAW biosensor on langasite." IEEE transactions on ultrasonics, ferroelectrics, and frequency control 51.11 (2004): 1404-1411.
Hechner, J., and W. Soluch. "Pseudo surface acoustic wave dual delay line on 41 YX LiNbO 3 for liquid sensors." Sensors and Actuators B: Chemical 111 (2005): 436-440.
Harding, G.L., et al. "Love wave acoustic immunosensor operating in liquid." Sensors and Actuators A: Physical 61.1 (1997):279-286.
Welsch, W., et al. "Immunosensing with surface acoustic wave sensors." Sensors and Actuators A: Physical 62.1-3 (1997):562-564.
Chi, Young Shik, et al. "A Noncovalent Approach to the Construction of Tween 20-Based Protein Microarrays." ChemBioChem 8.12 (2007): 1380-1387.

Fernandez-Sanchez, C., M. B. Gonzalez-Garcia, and A. Costa-Garcia. "AC voltammetric carbon paste-based enzyme immunosensors." Biosensors and Bioelectronics 14.12 (2000): 917-924.
Sun, Chong, et al. "Applications of antibiofouling PEG-coating in electrochemical biosensors for determination of glucose in whole blood." Electrochimica Acta 89 (2013): 549-554.
Chi, Young Shik, et al. "Asymmetrically Functionalized, Four-Armed, Poly (ethylene glycol) Compounds for Construction of Chemically Functionalizable Non-Biofouling Surfaces." Chemistry—An Asian Journal 4.1 (2009): 135-142.
Josse, Fabien and Zack Shana. "Analysis of shear horizontal surface waves at the boundary between a piezoelectric crystal and a viscous fluid medium." The Journal of the Acoustical Society of America 84.3 (1988): 978-984.
Cular, Stefan, et al. "Removal of nonspecifically bound proteins on microarrays using surface acoustic waves." IEEE Sensors journal 8.3 (2008): 314-320.
Singh, Reetu, Subramanian KRS Sankaranarayanan, and Venkat R. Bhethanabotla. "Enhancement of acoustic streaming induced flow on a focused surface acoustic wave device: Implications for biosensing and microfluidics." Journal of Applied Physics 107.2 (2010): 024503.
Sankaranarayanan, Subramanian KRS, et al. "Flow induced by acoustic streaming on surface-acoustic-wave devices and its application in biofouling removal: A computational study and comparisons to experiment." Physical Review E 77.6 (2008): 066308.
Singh, Reetu, Subramanian KRS Sankaranarayanan, and Venkat R. Bhethanabotla. "Orthogonal surface acoustic wave device based on langasite for simultaneous biosensing and biofouling removal." Applied Physics Letters 94.26 (2009): 263503.
Berkenpas, E., Paul Millard, and M. Pereira Da Cunha. "Detection of *Escherichia coli* O157: H7 with langasite pure shear horizontal surface acoustic wave sensors." Biosensors and Bioelectronics 21.12 (2006): 2255-2262.
Singh, Reetu, Subramanian KRS Sankaranarayanan, and Venkat R. Bhethanabotla. "Enhanced surface acoustic wave biosensor performance via delay path modifications in mutually interacting multidirectional transducer configuration: A computational study." Applied Physics Letters 95.3 (2009): 034101.
Subramanian KRS Sankaranarayanan, et al. "Flow induced by acoustic streaming on surface-acoustic-wave devices and its application in biofouling removal: A computational study and comparisons to experiment." Physical Review E 77.6 (2008): 066308.
Cular, Stefan, Venkat R. Bhethanaboltla, and Darren W. Branch. "Hexagonal surface acoustic wave devices for enhanced sensing and material characterization." IEEE Ultrasonics Symposium. 2005.
Cular, Stefan, Venkat R. Bhethanabotla, and Darren W. Branch. "Simultaneous surface manipulation and sensing in a biosensor using a hexagonal SAW device." AIChE Annual Meeting. 2006.

* cited by examiner

ORTHOGONAL SAW TRANSDUCERS ON SUBSTRATE FOR SIMULTANEOUS BIOFOULING REMOVAL AND BIOSENSING

CROSS REFERENCE TO RELATED APPLICATIONS

This application claims priority to U.S. provisional application entitled "ORTHOGONAL SAW TRANSDUCERS ON ST-QUARTZ FOR SIMULTANEOUS BIOFOULING REMOVAL AND BIOSENSING" having Ser. No. 62/107,787, filed Jan. 26, 2015, the entirety of which is hereby incorporated by reference.

STATEMENT REGARDING FEDERALLY SPONSORED RESEARCH OR DEVELOPMENT

This invention was made with government support under Grant Number 0801929 awarded by National Science Foundation. The government has certain rights in this invention.

BACKGROUND

The field of clinical diagnostics is interested in point-of-care testing (POCT) with miniaturized biosensors, where the sample is taken from the patient and placed onto a sensor in one step. The use of labels in sensing applications allows detection of analytes with sensitivity and specificity. However, sensing can take up long periods of time and detection cannot take place in real-time. In contrast, label-free sensing can provide fast, real-time detection of a biorecognition event that would be beneficial in POCT. However, current label-free techniques cannot differentiate between responses caused by specific and non-specific interactions. Thus, sensor performance is negatively affected with regard to ability to detect, sensitivity of the detection, and the dynamic range of the detection.

Sensing systems can utilize on a buffer solution containing an isolated antigen. However, these sensing systems cannot detect biomarkers in complex fluids, such as serum, urine, or blood. As such, it would be beneficial to make a biosensor that can sense biomarkers in complex fluids.

DESCRIPTION OF THE DRAWINGS

For a more complete understanding of the embodiments and the advantages thereof, reference is now made to the following description, in conjunction with the accompanying figures briefly described as follows.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions or positioning may be exaggerated to help visually convey certain principles. In the drawings, similar reference numerals between figures designate like or corresponding, but not necessarily the same, elements.

DETAILED DESCRIPTION

In the following paragraphs, the embodiments are described in further detail by way of example with reference to the attached drawings. In the description, well known components, methods, and/or processing techniques are omitted or briefly described so as not to obscure the embodiments.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

Surface acoustic wave devices can be used as direct, label-free biosensors that monitor the interaction between a receptor and its target in real time through changes in the properties of the travelling wave. The properties can include frequency, velocity, and amplitude. Energy dissipation while operating in liquid can be minimized using a shear-horizontal (SH) wave mode. Several substrates with defined crystal cuts, such as 36° YX lithium tantalate (LiTaO3), ST-Quartz, 41° YX lithium niobate (LiNbO3), and langasite, can be used in generating a shear-horizontal wave. These substrates can be used to meet the criterion and can be applied successfully in liquid sensing. Despite the advantageous properties of SH-surface acoustic wave (SAW) sensors, discrimination between specific and non-specific interactions is not possible. One approach to alleviate this problem can be to use a dual-delay line setup. In this case, one delay-line is used for sensing and the other is used as a reference. This allows elimination of environmental effects common to both delay-lines from the final sensor response. However, this requires increased circuit complexity and would not account for the randomness of non-specific surface binding. Another alternative to eliminate unwanted interactions is to create inert/resistant surfaces through modification. Common approaches include use of detergents, blocking proteins (BSA), or polymer films. Problems with these methods are increased setup time and costs, and compatibility issues with common sensing materials.

Rayleigh waves are not suitable for liquid sensing applications because mode conversion that occurs from liquid loading can cause severe attenuation. However, acoustic streaming induced by Rayleigh SAWs in contact with a liquid can remove proteins weakly attached to the surface. However, the substrate (128° YX LiNbO3) does not support a SH-SAW. Thus, integration of a Rayleigh SAW and an SH-SAW requires a different substrate. Coupled field finite element (FE) fluid structure interaction (FSI) can function as a mechanisms of ultrasonic removal of non-specifically bound proteins. A SAW direct force can overcome adhesive forces (van der waals and electrical double layer), and hydrodynamic forces (drag and lift) to prevent particle re-attachment.

Definitions

As used herein, "specifically binds" or "specific binding" refers to binding that can occur between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, "specific binding" can occur between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "non-specific binding" or "non-specifically binds" refers to binding that occurs between a target species and another species that is not the specific binding partner to the target species and/or a substrate. "non-specific binding" or "non-specifically binds" can also refer to the binding that occurs between a non-target species and a specific binding partner of a non-target species, another species that is not the specific binding partner of the non-target species, the specific binding partner of the target species, and/or a substrate.

As used herein, "capture molecule" refers to a molecule that is configured to specifically bind one or more target molecules of interest. A capture molecule can be a nucleotides, antibody, antigen, apatmer, affibody, polypeptides, peptides, or combinations thereof that specifically bind one or more target molecules.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "peptide" refers to two or more amino acids where the alpha carboxyl group of one amino acid is bound to the alpha amino group of another amino acid. Strings of 10 or more amino acids are also referred to herein as "polypeptides" or "proteins".

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "deoxyribonucleic acid (DNA)" and "ribonucleic acid (RNA)" generally refer to any polyribonucleotide or polydeoxribonucleotide, which can be unmodified RNA or DNA or modified RNA or DNA. RNA can be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), microRNA (miRNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, polynucleotide as used herein refers to triple-stranded regions comprising RNA or DNA or both RNA and DNA. The strands in such regions can be from the same molecule or from different molecules. The regions can include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotide" as that term is intended herein.

As used herein, "affibody" refers to an engineered protein that is an antibody mimetic and can specifically bind a target molecule, and is based on a three-helix bundle domain, where each of the three helixes contains a polypeptide having about 58 amino acids.

As used herein, "target molecule" can refer to any measurable molecule or compound of interest, including but not limited to polynucleotides and polypeptides, other organic compounds, and inorganic compounds.

As used herein "attached" as applied to capture molecules of an array refers to a covalent interaction, non-covalent interaction, or other bond between a surface of the substrate and the capture molecule so as to immobilize the capture molecule on the surface of the substrate. Such non-covalent interactions include by are not limited to, entrapment by the surface substrate, ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-$\pi$ interactions, anion-$\pi$ interactions, polar $\pi$-interactions, and hydrophobic effects.

DISCUSSION

Described herein is a dual function surface acoustic wave (SAW) device that can remove non-specific binding molecules in a bioassay. The dual function SAW device can include a substrate with a surface. As an example, the substrate can be made of ST-Quartz. On the surface of the substrate, a first and a second set of input and output transducers can be formed orthogonal to each other. A first set of input and output transducer can be aligned with the x-axis of the substrate and orthogonal to the z-axis of the substrate. This first set of input and output transducers can excite a Rayleigh SAW. A second set of the input and output transducers can be formed orthogonal to the x-axis of the substrate and aligned with the z-axis of the substrate. The second set of the input and output transducers can excite a shear wave, such as a surface skimming bulk wave (SSBW). The shear wave can be horizontally polarized.

The input of the input and output transducers can be conjugate matched to the output of the input and output transducers. In one embodiment, only the input and output transducers that excite a Rayleigh SAW are conjugate matched. The substrate can include a fluid retention mechanism parallel to the substrate. In one embodiment, the fluid retention mechanism is an o-ring seal. When a fluid sample is added to the dual function SAW device, the fluid sample can be laterally bound by the fluid retention mechanism. The fluid sample can be vertically supported by the surface of the substrate. In one embodiment, the fluid retention mechanism covers the surface of the substrate and provides vertical support to the fluid sample.

The dual function SAW device can remove non-specific bindings in the bioassay by applying a shear wave and a Rayleigh wave to a fluid sample. The shear wave can be applied orthogonal to the x-axis of the substrate. The shear wave can pass through the fluid sample. The shear wave can be excited or enabled before a fluid sample is added to the dual function SAW device. The shear wave can be excited or enabled by applying power or a signal across contacts corresponding to the second set of input and output transducers. In one embodiment, a first component of the fluid sample is added to the dual function SAW device before the shear wave is excited and then subsequently a second component of the fluid sample is added. The second component of the fluid sample can be added through a dropper method. The shear wave can be excited or enabled for a period of time corresponding to the assay. As a non-limiting example, an input and output transducer can be enabled for ten minutes to perform the assay.

To remove the non-specific bindings in the fluid sample, a Rayleigh SAW wave can be excited parallel to the x-axis of the substrate. The Rayleigh SAW wave can be transmitted through the fluid sample. The Rayleigh SAW can be excited or enabled by applying power or a signal across contacts corresponding to the first set of input and output transducers.

In some embodiments, the bioassay is not a continuous flow assay. While the Rayleigh SAW is enabled, the fluid sample can be rinsed to remove the non-specific binding molecules. In other embodiments, the bioassay is a continuous flow assay and the non-specific binding molecules can be filtered out while the Rayleigh SAW is enabled. The shear wave and the Rayleigh SAW can be applied simultaneously. By applying them simultaneously, the shear wave can facilitate measuring a phase shift caused by a change in the fluid sample caused by the Rayleigh SAW.

The fluid sample can be contained on the surface of the substrate using a fluid retention mechanism, such as an o-ring seal. The fluid retention mechanism can be positioned parallel to the substrate. In some embodiments, a capture molecule is attached to the surface of the substrate. The capture molecule can specifically bind to a target molecule. The capture molecule can be selected based on what target molecule the bioassay is intended to detect. As an example, to detect a specific target molecule, a capture molecule that can specifically bind to the target molecule can be selected. The fluid sample can be a blood sample, a urine sample, a saliva sample, a mucus sample, or other fluids.

Figure 1:
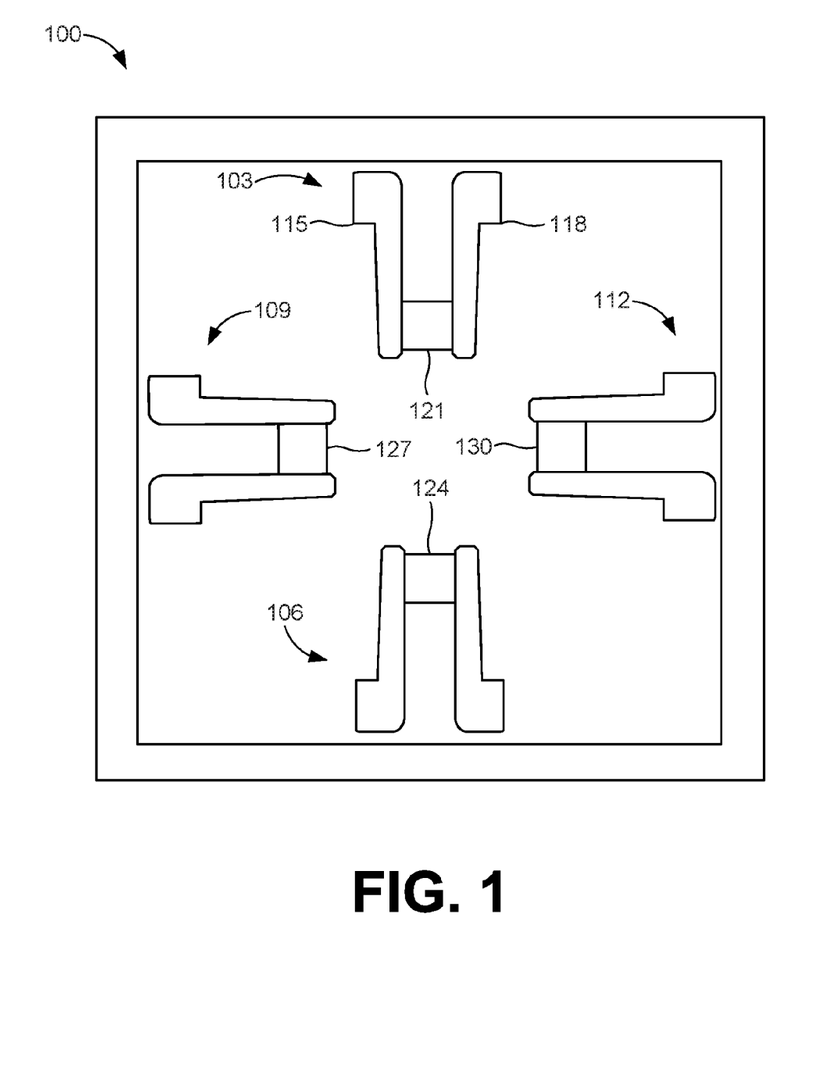
FIGS. 1 and 2 are drawings of a dual function surface acoustic wave device according to various embodiments of the present disclosure.

With reference to FIG. 1, shown is a dual function SAW device 100 according to various embodiments. The dual function SAW device 100 includes an input transducer 103, an output transducer 106, an input transducer 109, and an output transducer 112. Each of the transducers 103, 106, 109, and 112 can include a first terminal 115 and a second terminal 118. The input transducer 103 can include a sensing element 121, and the input transducer 109 can include a sensing element 127. The output transducer 106 can include an emitting element 124, and the output transducer 112 can include an emitting element 130.

The output transducers 106 and 112 can convert an electrical signal into acoustical waves, such as a polarized transversal wave, that can travel parallel to the sensor surface along a guiding layer using the emitting elements 124 and 130. The guiding layer can enable all the acoustic energy to stay concentrated instead of propagating over the entire surface. As an example, the emitting element 124 can excite Rayleigh surface acoustic waves when a voltage is applied across the first terminal 115 and the second terminal 118 of the output transducer 106. According to one embodiment, the voltage can be applied as a signal with an amplitude and a period.

As another example, the emitting element 130 can excite a shear wave when a voltage is applied across the first terminal 115 and the second terminal 118 of the output transducer 112. According to one embodiment, the input and output transducers 103 and 106 and input and output transducers 109 and 112 are made up of input and output interdigital transducers (IDTs) with a guiding layer between the input and output element of each IDT.

At the other end of the device, the input transducer 103 or 109 receives the wave and converts it back into an electrical signal. As an example, the input transducers 103 and 109 can convert an acoustical wave into an electronic signal using the sensing elements 121 and 127. Sensing elements 121 and 127 can be used to sense acoustic waves that are sensitive to changes in mass, density, viscosity, and acoustic coupling. For example, the fluid sample can alter properties of the acoustical wave when the changes occur, and the sensing elements 121 and 127 can sense the acoustical wave after the alteration occurs.

The dual function SAW device 100 can utilize the ability of a material, such as quartz, to generate acoustic waves. In particular, a surface acoustic wave is an acoustic, mechanical wave propagating within the confines of the surface of a crystal. The material of the substrate in the dual function SAW device 100 can generate both a Rayleigh SAW and a shear horizontal SAW (SH-SAW). As one example, both a Rayleigh SAW and an SH-SAW can be generated on an ST-Quartz substrate. The input and output transducers 103 and 106 can generate a Rayleigh SAW and the input and output transducers 109 and 112 can generate an SH-SAW. When a SAW comes in contact with something on the surface, the wave phase, velocity, and/or amplitude can be greatly affected.

The Rayleigh wave generated by the input and output transducers 103 and 106 can detach and remove non-specifically bound proteins in a fluid sample from the surface of a substrate while leaving specifically bound proteins intact. This removal mechanism uses a SAW to detach and remove a bound protein. As an example, a Rayleigh waves generated on ST-Quartz can remove non-specific bound proteins while maintaining specific binding between antigen and antibody.

As shown in FIG. 1, a first SAW delay line formed by the input and output transducers 103 and 106 can be placed orthogonal to a second SAW delay line formed by the input and output transducers 109 and 112. By placing the two SAW delay lines orthogonal to each other on a substrate, such as an ST-Quartz substrate, the dual function SAW device 100 can simultaneously detect mass absorption and de-absorption and can remove proteins non-specifically bound to the surface of a fluid sample. The first delay-line formed by the input and output transducers 103 and 106 can be oriented orthogonal to the crystalline x-axis of a substrate and can generate a Rayleigh wave. The second delay-line formed by the input and output transducers 109 and 112 can be aligned orthogonal to the crystalline z-axis of the substrate and can generate a surface skimming bulk wave (SSBW), which is an SH-SAW.

The dual function SAW device 100 can be fabricated by a photolithography process and a metal lift-off procedure. The frequency response for each delay line can be measured using a network analyzer and compared to theoretically derived values to verify if the expected wave modes are generated. Theoretical calculations can be based on each mode's acoustic velocity, such as 3158 m/sec for a Rayleigh wave and 5060 m/sec for an SSBW wave, and acoustic wavelength, such as 40 µm. The theoretical calculations can be compared to the measured values to determine discrepancies between the values caused by mass loading of the transducers and misalignment of the transducers with the crystalline axes.

Figure 2:
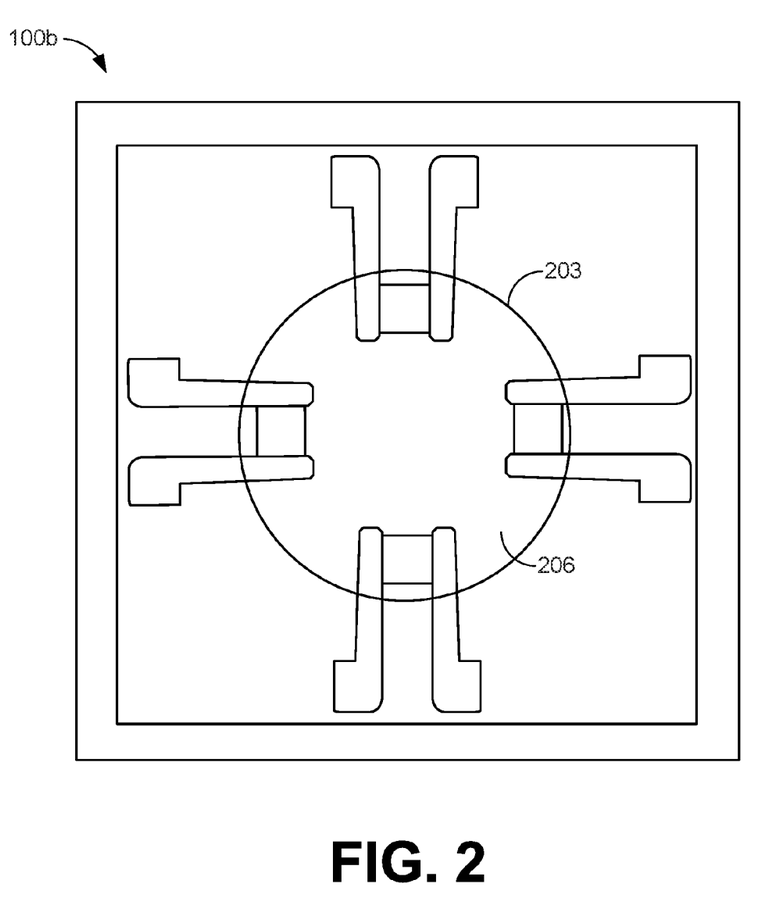

With reference to FIG. 2, shown is a dual function SAW device 100b according to various embodiments. The dual function SAW device 100b includes a fluid retaining mechanism 203 and a fluid sample 206. The fluid retaining mechanism 203 can be a cylindrical protrusion that extends outward from a substrate of the dual function SAW device 100b. In other embodiments, the fluid retaining mechanism 203 is a different shape, such as a rectangular protrusion among other shapes.

In one embodiment, the fluid retaining mechanism 203 is a mechanical gasket in the shape of a torus, such as an o-ring. The fluid retaining mechanism 203 can be sealed with regard to the substrate, such that fluid cannot pass between the fluid retaining mechanism 203 and the substrate. The fluid retaining mechanism 203 can have a radius being larger or smaller than shown in FIG. 2. In some embodiments, the fluid retaining mechanism 203 has a radius that causes the fluid retaining mechanism 203 to extend outside of the input and output transducers 103, 106, 109, and 112. In another embodiment, the radius is such that the fluid retaining mechanism 203 is such that the fluid retaining mechanism is inside of the input and output transducers 103, 106, 109, and 112 without touching them.

The fluid sample 206 can be laterally supported by the fluid retaining mechanism 209 and vertically supported by the substrate of the dual function SAW device 100b. In one embodiment, the fluid sample 206 can be added into a reservoir created by the fluid retaining mechanism 203 and the substrate using a droplet method. A droplet method can allow the dual function SAW device 100b to isolate the removal process due to SAW induced acoustic streaming. With the droplet method, removal will not occur due to the fluid sample 206 flowing. According to one embodiment, a droplet method is used instead of a flow through system to isolate removal due to SAW induced acoustic streaming. Using the droplet method can eliminate the possibility of removal occurring from forces due to the flowing fluid.

According to one embodiment, the removal of non-specifically bound proteins can be measured by the dual function SAW device 100b by first applying a first fluid sample to a second fluid sample and waiting for the samples to settle. For example, a 5 µL drop of BSA (200 µg/mL) in DI water can be added into a DI water fluid sample and the phase shift can be monitored in real time. In another example, human blood or urine can be used. Before applying a BSA solution, a fluid sample of DI water can be placed on the substrate of the dual function SAW device 100b. In one example, the fluid sample of DI water is 15 µL and covers an area of 15.9 mm$^2$. The use of a fluid retaining mechanism 203 can prevent the liquid from spreading.

To verify no appreciable phase shift occurs from adding liquid volume of the first sample to the second sample, an experiment involving adding 5 µL of DI water can be performed. Measurements of a phase from the input and output transducers 109 and 112 can be taken to determine removal of the non-specifically bound molecules. The input and output transducers 103 and 106 can excite a Rayleigh wave, and the measurements of phase can be taken again to verify removal of the non-specific molecules bindings. According to one embodiment, the non-specific molecules are proteins.

Figure 3:
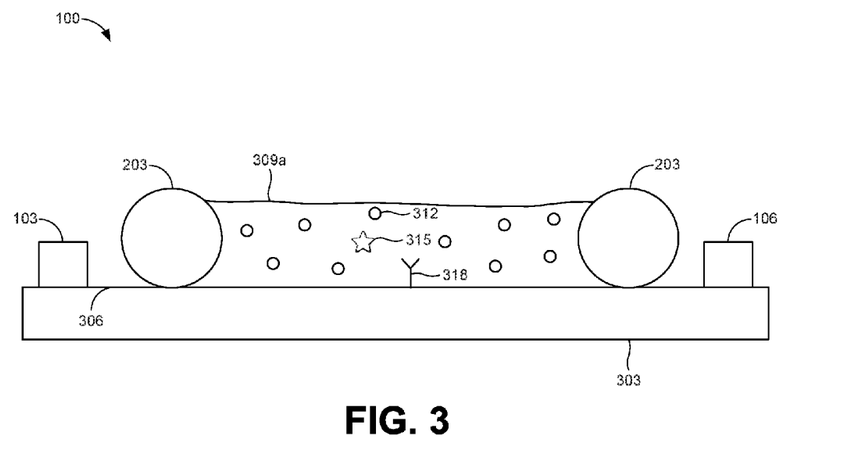
FIGS. 3-5 are drawings of a cross section of a dual function surface acoustic wave device according to various embodiments of the present disclosure.

Turning to FIG. 3, shown is a cross section of a dual function SAW device 100 according to various embodiments of the present disclosure. The dual function SAW device 100 can include a substrate 303 with a surface 306, a fluid sample 309a containing one or more non-target molecules 312, a target molecule 315, and a capture molecule 318. The dual function SAW device 100 can also includes input transducer 103, output transducer 106, and fluid retaining mechanism 203. An input transducer 109 and output transducer 112, as shown in FIGS. 1 and 2, are included in dual function SAW device 100, but are not shown in the cross section.

In one embodiment, the fluid sample 309a was made by adding a first fluid sample into a second fluid sample. The first fluid sample can be added to the second fluid sample using the dropper method. The first fluid sample can include the non-target molecules 312 and target molecule 315, and the second sample can include the capture molecule 318.

In another embodiment, the capture molecule 318 can be located on the surface 306 of the substrate 303. A fluid sample 309a including the target molecule 315 and non-target molecules 312 can be subsequently added to the dual function SAW device 100. As an example, a dual function SAW device 100 can be manufactured without fluid sample 309a or target molecule 315. The dual function SAW device 100 can be packaged and shipped to doctor's offices or other locations without the fluid sample 309a, but including the capture molecule 318. A fluid sample 309a, such as blood or urine from a patient, can be collected and added to the dual function SAW device 100 at a doctor's office or hospital. The non-target molecule 312 and target molecules 315 can be within the blood or urine of the patient. In this example, the dual function SAW device 100 can be used to test if a patient has a target molecule 315 within the patient's blood or urine.

The capture molecule 318 can specifically bind to the target molecule 315. According to one embodiment, none of the non-target molecules 312 can specifically bind with either the target molecule 315 or the capture molecule 318. The target molecule 315 can move within the fluid sample 309a using natural locomotion. In one embodiment, the dual function SAW device 100 is shaken to expedite mixing of the fluid sample 309a. When the target molecule 315 comes in contact with capture molecule 318, the target molecule 315 and capture molecule 318 can specifically bind to one another.

According to one embodiment, while the fluid sample 309a is added to the dual function SAW device 100, a SH-SAW is excited from the output transducer 112 and characteristics of the SH-SAW are monitored. In one example, the SH-SAW can be monitored by the input transducer 109. The input transducer 109 can be communicably coupled to a computing device, such as a processor to facilitate the monitoring. In another example, the SH-SAW can be monitored by a network analyzer. The network analyzer can include a sensor connected to the surface 306 of the substrate 303 or can be held or affixed within the fluid sample 309a. A measurement of fluid sample 309a can vary based on the characteristics, such as weight, of the non-target molecules 312, the target molecule 315, and the capture molecule 318.

Figure 4:
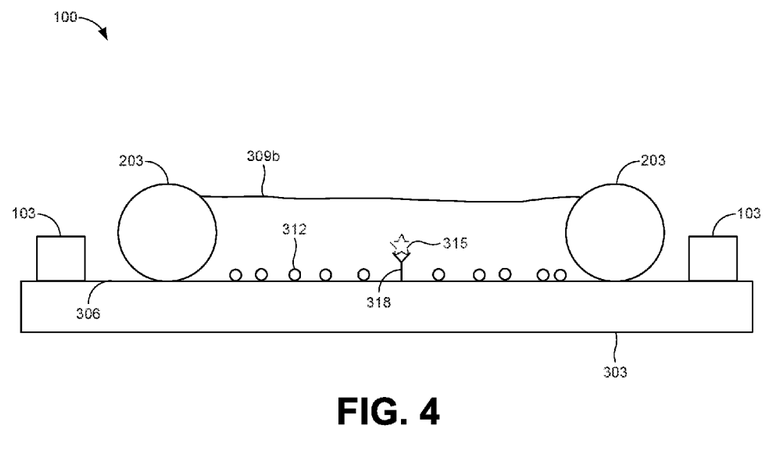

With reference to FIG. 4, shown is a cross section of a dual function SAW device 100 according to various embodiments of the present disclosure. The fluid sample 309b illustrates the non-target molecules 312 attached to the surface 306 through a weak non-specific bound. The fluid sample 309b also illustrates the target molecule 315 bound to the capture molecule 318.

The fluid sample 309b can represent the fluid sample 309a (FIG. 3) after the fluid sample 309a sits for a period of time. As an example, after adding fluid sample 309a to the dual function SAW device 100, the fluid sample 309a can sit for ten minutes to allow the fluid sample 309a to settle. During that period of time, the non-target molecules can non-specifically bind to the surface 306 of the substrate 303 and the target molecule 315 can specifically bind to capture molecule 318, as shown in the fluid sample 309b.

Figure 5:
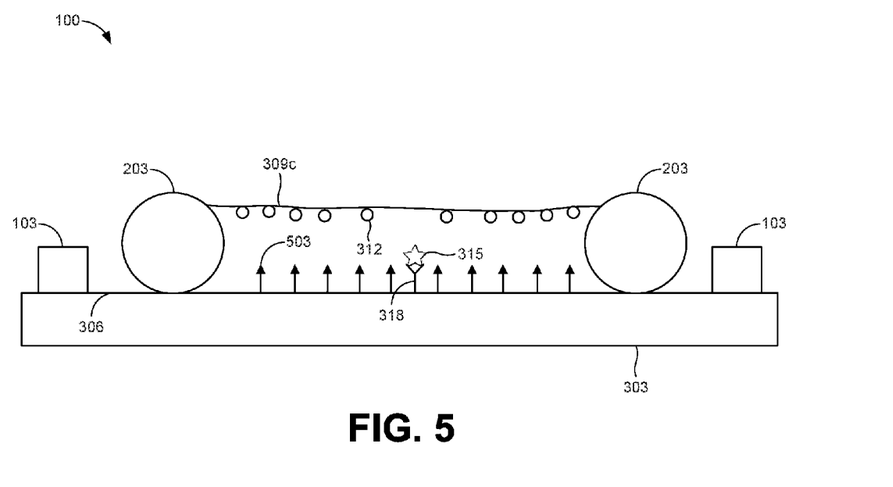

With reference to FIG. 5, shown is a cross section of a dual function SAW device 100 according to various embodiments of the present disclosure. The fluid sample 309c can represent the fluid sample 309b (FIG. 4) after a Rayleigh wave has been excited through the fluid sample 309b. Once the target molecule 315 has had time to bind to capture molecule 318, a Rayleigh wave can be used to separate and remove the non-specifically bound non-target molecules 312 from the path of the SH-SAW. The Rayleigh wave can generate an upward force 503 within the fluid sample 309c. The upward force 503 can be strong enough to separate the weaker non-specific bindings from the non-target molecules 312 and lift the non-target molecules 312 out of the path of the SH-SAW. However, the upward force 503 can be weak enough to not disrupt the stronger specific binding between the target molecule 315 and capture molecule 318.

The force 503 from the Rayleigh wave can move the non-target molecules 312 to the top of the fluid sample 309c. According to one example, the Rayleigh wave moves to the non-target molecules 312 out of the range of the SH-SAW, such that the non-target molecules 312 are not measured. After the Rayleigh wave removes the non-target molecules 312, measurements of the SH-SAW can be captured. According to one embodiment, the measurement of the fluid sample 309c can differ based on whether the target molecule 315 is present in the fluid sample 309c. The dual function SAW device 100 can notify a user if the target molecule 315 is present in the fluid sample. For example, the dual function SAW device 100 can power a light emitting diode if the target molecule 315 is detected.

According to one example, after the fluid sample 309a is introduced, the phase of the SH-SAW decreases, which corresponds to mass being absorbed onto the surface. In this example, the phase can continue to decrease for 600 seconds after the fluid sample 309a is introduced. At this time, the Rayleigh wave can be excited by applying an RF signal (15 dBm, 78.5 MHz) to the input and output transducers 103 and 106. After a delay, such as after 100 seconds, the phase can shift upwards due to mass being removed from the surface to a distance exceeding that where SH-SAW sensing is effective. In this example, the absolute phase shift due to protein absorbing to the surface is approximately 0.3°. Removal of the non-target molecules 312 from the surface 306 can result in an absolute phase shift of about 0.2°. The discrepancy between the phase shift obtained due to adsorption and that obtained due to removal indicates that all the mass was not removed from the surface.

The reflected power can be decreased by conjugate matching the input transducer 103 with the output transducer 106. According to one example, the use of identical matching circuits at the input and output ports of a Rayleigh SAW delay line decreased insertion loss by 17.732 dB. By reducing the insertion loss through conjugate matching of the input and output transducers 103 and 106, the power required on the input signal for removal can be reduced. As an example, when the input and output transducers 103 and 106 are conjugate matched, an amplification of the input signal required for removal can be reduced substantially. Reducing the power through conjugate matching can greatly reduce the heat of the dual function SAW device 100.

When conjugate matching is used, the phase measured of the SH-SAW changes when the Rayleigh wave is excited. According to one example embodiment, RF power (15 dBm, 78.5 MHz) was applied to the input and output transducers 103 and 106 after approximately 600 seconds when the signal had stabilized. In this example, the phase immediately increased due to removal of the non-targeted molecules from the surface 306. The increase in phase can exceed the phase prior to the non-target molecules 312 and target molecules 315 being introduced. This change can be attributed to decreased mass loading due to atomization or evaporation of some liquid because of the increased acoustic energy.

In the above example embodiment, at approximately 810 seconds, the RF power to the Rayleigh wave delay line was turned off. Analysis of the phase measurements at this point indicates all the adsorbed mass is removed from the surface beyond the height where SH-SAW detection is possible. If the power to the Rayleigh wave delay line is terminated, the phase can decrease and eventually returns to the phase value occurring before the Rayleigh wave was enabled, as shown in FIG. 4. In this example, the phase shift due to adsorption was ~0.3°. This value is consistent with the result from other experiments. However, the phase shift due to removal was ~0.5-0.6°, which demonstrates complete removal of non-target molecules 312. The return of the phase curve to pre-RF input values is evidence that non-target molecules 312 re-adsorbed onto the surface. The non-target molecules 312 can be permanently removed by a rinsing step or continuous flow during operation.

Figure 6:
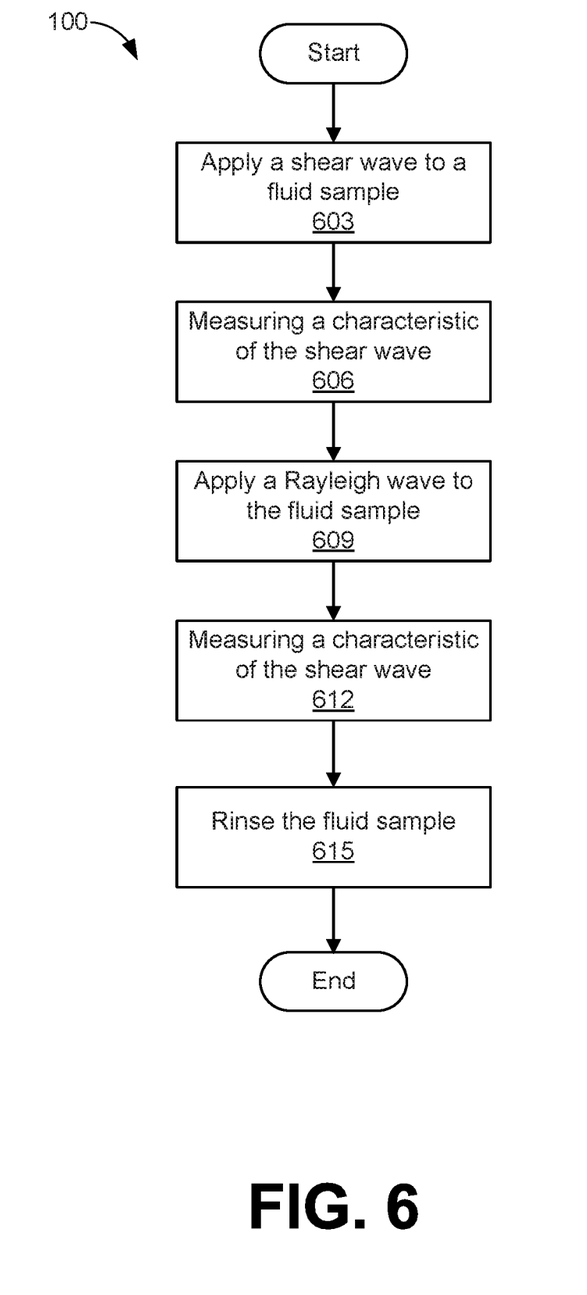
FIG. 6 is a flowchart illustrating one example of functionality implemented as portions of the dual function surface acoustic wave device according to various embodiments of the present disclosure.

Moving on to FIG. 6, shown is a flowchart illustrating example operations of a dual function SAW device 100. In certain aspects, the flowchart of FIG. 6 can be viewed as depicting example elements of a method implemented on the dual function SAW device 100 of FIG. 1. Although the processes of FIG. 6 are described in connection with the dual function SAW device 100, other devices can operate according to the processes illustrated. Further, it should be understood that the flowchart of FIG. 6 provides only examples of different functional or process arrangements that may be employed according to the embodiments described herein. Different elements in the flowchart of FIG. 6 can be omitted or occur in a different order than shown.

Beginning at step 603, the process involves applying a shear wave to a fluid sample. For example, dual function SAW device 100 can excite an SH-SAW through a fluid sample 206 (FIG. 2) using input and output transducers 109 and 112. A phase of the SH-SAW can vary based on the fluid sample 206. As an example, if the fluid sample 206 includes non-specifically bound molecules, the phase can differ in comparison to the non-specifically bound molecules being removed.

Next at step 606, a characteristic of the shear wave can be measured. For example, a phase of a SH-SAW can be measured. The measurement of the phase can correspond to one or more characteristics of the fluid sample 206. The measurement can correspond to the fluid sample 206 when a Rayleigh wave is not applied. In one example, the measurement corresponds to a fluid sample 206 before a second component is added to the fluid sample 206. In one embodiment, measurements can be captured before and after a second component is added to the fluid sample 206. The second component can include the target molecule 315 and non-target molecules 312. An input and output transducer 109 and 112 can output and measure the SH-SAW.

In step 609, a Rayleigh wave is applied to the fluid sample. For example, the input and output transducers 103 and 106 can excite a Rayleigh SAW that is applied through the fluid sample 206. The Rayleigh SAW can break the bonds of non-specifically bound non-target molecules 312. The Rayleigh SAW can also remove these non-target molecules 312 from the path of the SH-SAW by applying an upward force. The force from the Rayleigh SAW can lift the non-target molecules 312 toward the top of the fluid sample 206. In one example, the lift force from the Rayleigh SAW is weak enough not to break the specifically bound target molecule 315, which is bound to the capture molecule 318

Turning to step 612, similar to step 606, a characteristic of the shear wave can be measured. For example, a phase of the SH-SAW can be measured after the removal of the non-target molecules 312. The measurement of the phase can correspond to one or more characteristics of the fluid sample 206 without the non-target molecules 312. In one example, the measurement can be determined while the Rayleigh SAW is being excited by the input and output transducers 103 and 106. In another example, the measurement can be determined after a flushing of the fluid sample 206, such as the flushing described in step 615. When the measurement is determined after a flushing of the fluid sample 206, the Rayleigh SAW can be disabled prior to the measurement being taken.

At step 615, the fluid sample 206 can be rinsed. As an example, another fluid can be passed over the top of the fluid sample 206 to flush the non-specifically bound non-target molecules from the fluid sample 206. The Rayleigh wave can generate a force the separate the non-specifically bound non-target molecules 312 and force the non-target molecules 312 them to the top of the fluid sample 206. Once the non-target molecules 312 are located at the top of the fluid sample 206, a flushing of the fluid sample 206 can remove the non-target molecules 312. The fluid that passes over the top of the fluid sample 206 can be a buffering solution or another solution.

In another embodiment, a capacity of the fluid reservoir can be altered to reduce the volume of the fluid sample 206.

The excess volume can correspond to the fluid at the top of the fluid sample 206. The excess volume of the fluid sample 206 can be flushed by overflowing over the fluid retaining mechanism 203 (FIG. 2). In one embodiment, a bottom of fluid retaining mechanism 203 can be raised to reduce the capacity of the fluid reservoir. In another embodiment, a retaining edge of the fluid retaining mechanism 203 can be lowered to reduce the capacity of the fluid reservoir. In yet another embodiment, a radius or one or more dimensions of the fluid retaining mechanism 203 can be reduced to reduce the capacity of the fluid reservoir.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A dual function surface acoustic wave (SAW) device configured for use in removing non-specific binding in a bioassay, the device comprising:
   a first set of input and output transducers configured to apply a shear wave orthogonal to an x-axis of a substrate through a fluid sample;
   a second set of input and output transducers configured to apply a Rayleigh surface acoustic wave parallel with the x-axis of the substrate through the fluid sample;
   a flushing fluid, wherein the dual function SAW device is configured to rinse the fluid sample on the substrate via the flushing fluid while the Rayleigh surface acoustic wave and the shear wave are being applied to filter out a plurality of non-specific binding molecules; and
   a computing device configured to measure a phase shift of the shear wave caused by a change in the fluid sample resulting from a binding of a target molecule to a capture molecule.

2. The dual function SAW device of claim 1, wherein at least one of: the first set of input and output transducers or the second set of input and output transducers are interdigital transducers (IDT).

3. The dual function SAW device of claim 1, wherein the first set of input and output transducers are aligned orthogonal to a x-axis of the substrate, and the second set of input and output transducers are aligned with the x-axis of the substrate, the x-axis being parallel to a direction of wave propagation.

4. The dual function SAW device of claim 1, wherein the substrate is an ST-Quartz substrate.

5. The dual function SAW device of claim 1, wherein the shear wave is horizontally polarized.

6. The dual function SAW device of claim 1, wherein the shear wave is a surface skimming bulk wave.

7. The dual function SAW device of claim 1, wherein an input of the first set of input and output transducers are conjugate matched to an output of the first set of input and output transducers.

8. The dual function SAW device of claim 1, further comprising a fluid retention mechanism positioned parallel to the substrate.

9. The dual function SAW device of claim 8, wherein the fluid retension mechanism is an o-ring seal.

10. The dual function SAW device of claim 8, further comprising a liquid laterally bound by the fluid retention mechanism.

11. The dual function SAW device of claim 1, wherein the capture molecule is bound to the substrate.

12. A method of removing non-specific binding in a bioassay comprising:
  applying, via a first set of input and output transducers, a shear wave orthogonal to an x-axis of a substrate through a fluid sample;
  applying, via a second set of input and output transducers, a Rayleigh surface acoustic wave parallel with the x-axis of the substrate through the fluid sample;
  rinsing the fluid sample on the substrate while the Rayleigh surface acoustic wave and the shear wave are being applied to filter out a plurality of non-specific binding molecules; and
  measuring a phase shift of the shear wave caused by a change in the fluid sample resulting from a binding of a target molecule to a capture molecule.

13. The method of claim 12, wherein the bioassay is not a continuous flow assay.

14. The method of claim 12, wherein the shear wave and the Rayleigh surface acoustic wave are simultaneously applied.

15. The method of claim 12, wherein the fluid sample is contained on the surface of the substrate within an o-ring seal positioned parallel to the substrate.

16. The method of claim 12, wherein the capture molecule is bound to the substrate.

17. The method of claim 12, wherein the capture molecule is configured to specifically bind the target molecule.

18. The method of claim 12, wherein the fluid sample is at least one of: a blood sample, a urine sample, a saliva sample, or a mucus sample.

19. The method of claim 12, wherein an input of the first set of input and output transducers are conjugate matched to an output of the first set of input and output transducers.

20. The method of claim 12, wherein the phase shift further results from filtering out the plurality of non-specific binding molecules by rising the fluid sample.

* * * * *